United States Patent [19] [11] 4,410,854
Kroneisen et al. [45] Oct. 18, 1983

[54] FLAME IONIZATION DETECTOR

[75] Inventors: Armin Kroneisen, Frankfurt; Gerd Zornig, Steinbach, both of Fed. Rep. of Germany

[73] Assignee: Hartmann & Braun Aktiengesellschaft, Frankfurt, Fed. Rep. of Germany

[21] Appl. No.: 284,332

[22] Filed: Jul. 17, 1981

[30] Foreign Application Priority Data

Jul. 23, 1980 [DE] Fed. Rep. of Germany ....... 3027863

[51] Int. Cl.³ ............................................ G01N 27/62
[52] U.S. Cl. .................................... 324/468; 324/464
[58] Field of Search ................ 324/459, 464, 467, 468

[56] References Cited

U.S. PATENT DOCUMENTS 2,994,035 7/1961 Feifel .................................... 324/464
3,080,754 3/1963 Johnson .............................. 324/464
3,713,773 1/1973 Fontijn ................................ 324/464
4,368,431 1/1983 Rohr .................................... 324/464

OTHER PUBLICATIONS

J. Fackrell, "A Flame Ionisation Detector for Measuring Fluctuating Concentration", J. Phys. E. Sci Instrum, vol. 13, No. 8, Aug. 1980, Printed in Great Britain, pp. 888-893.

Primary Examiner—Michael J. Tokar
Attorney, Agent, or Firm—Ralf H. Siegemund

[57] ABSTRACT

The flame ionization detector includes basically a nozzle for a measuring gas fuel gas mixture and is coaxially disposed to a target electrode. Materials and dimensions for these components are critical and include a platinum metal nozzle tip, a noble metal surface target electrode, a limited range for the nozzle duct diameter, a limited range for the relative position between the nozzle tip and the lower end of the target electrode, and angle ranges for conical nozzle contour surfaces.

7 Claims, 2 Drawing Figures

FLAME IONIZATION DETECTOR

BACKGROUND OF THE INVENTION

The present invention relates to a flame ionization detector.

Flame ionization detectors are, for example, constructed to include a cylindrical case containing a burner nozzle having a cylindrical gas duct and being made of corrosion-proof material. An essentially cylindrical target electrode is disposed coaxially to the nozzle. The bottom structure of the case is provided with inlet ducts for the fuel gas, for the measuring gas as well as for air needed for combustion.

A detector as described is, for example, disclosed in German printed patent application No. 2 342 333 (published in 1974 and being based on a patent application in Great Britain, Ser. No. 39733-72 of Aug. 25, 1972). A detector of this type could, for example, be used for measuring the concentration of carbon in hydrocarbons contained in the exhaust fumes for combustion engines.

Existing and available equipment in that field of art, however, exhibits rather widely varying measuring results. In some instances, the measured values are just incorrect; also, in these and other instances, the measured values could not be reproduced. Even if the measuring gas contains just one hydrocarbon compound and none other, the measuring results were found to vary significantly. The detectors had different responses. Conceivably then, the instrument had undiscovered design flaws.

DESCRIPTION OF THE INVENTION

It is an object of the present invention to provide a new and improved flame ionization detector which will yield more stable measuring results.

It is a particular object of the present invention to provide a new and improved flame ionization detector which is sufficiently accurate so that the carbon equivalent of any and all hydrocarbons in the measuring gas can be detected at an error rate not greater than ±5% in relation to the absolute content of such hydrocarbon of hydrocarbons within a range of concentration of not greater than 10% methane equivalent, independent from the composition of the host gas and its constituents; the measuring result should, in particular, not exhibit a so-called oxygen error.

It is a feature of the present invention to construct an improved flame ionization detector under retention of the use of a burner nozzle with a conical tip and being made of corrosion-proof material and an essentially cylindrical target electrode. It was discovered, however, that these elements must have particular critical dimensions, at least as far as dimensional ranges are concerned.

In accordance with the preferred embodiment of the present invention, it is suggested to provide a measuring gas-fuel gas duct in the nozzle to have a diameter of from 0.3 mm to 0.5 mm. The nozzles body or stem is to have a cylindrical or conical configuration with an apex angle not exceeding 14°, and the nozzle tip is to be made of a platinum metal or of one of its alloys, with an apex angle smaller than 90° but larger than the apex angle of the nozzle stem and at a base diameter not exceeding 1.0 mm, but not much smaller in view of the size of the duct passing through. The target electrode is to be made of corrosion-proof material which includes a metal, preferably a noble metal surface, and has an inner diameter of from 6 mm to 15 mm. The upper nozzle tip end should not penetrate deeper than 3 mm into the target electrode, nor should these two ends be farther apart than approximately 15 mm.

Additionally, the measuring gas and, particularly, the fuel gas and combustion air should flow within certain limits, 2-10 milliliters-per-minute measuring gas, normalized for a pressure of 760 torr at a temperature of 0° C. (Nml/min), 200 to 250 Nml/min air, and from 42 to 48 Nml/min. $H_2$. If the fuel is diluted with helium, a constant helium flow of 70 Nml/min should not be exceeded.

DESCRIPTION OF THE DRAWINGS

While the specification concludes with claims, particularly pointing out and distinctly claiming the subject matter which is regarded as the invention, it is believed that the invention, the objects and features of the invention, and further objects, features and advantages thereof, will be better understood from the following description taken in connection with the accompanying drawings, in which:

Figure 1:
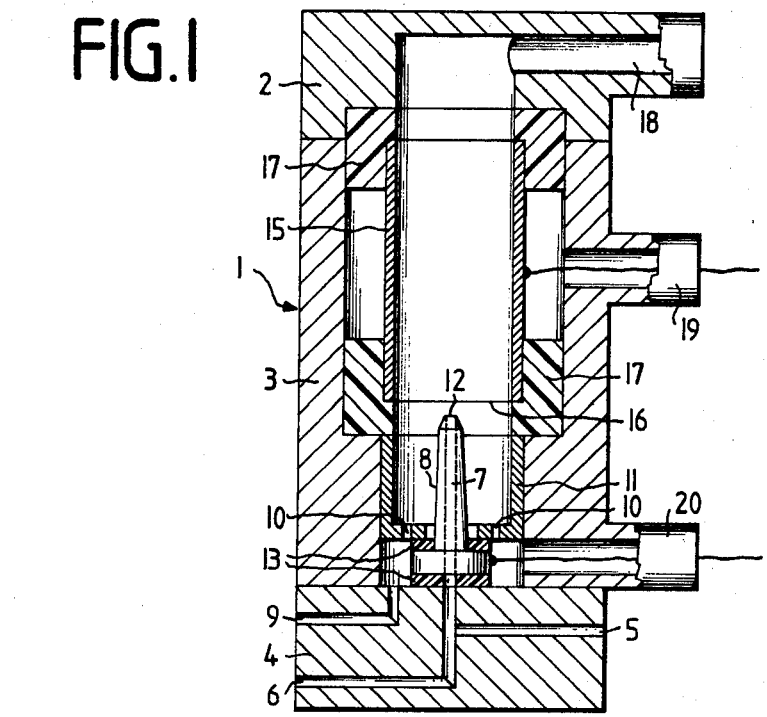
FIG. 1 illustrates a section view, on a slightly enlarged scale, of a flame ionization detector constructed in accordance with the preferred embodiment of the present invention for practicing the best mode thereof.

Proceeding now to the detailed description of the drawings, the flame ionization detector as depicted therein includes a case 1 being comprised of three parts; a top and cover part 2, a basically cylindrical part 3, and a bottom part 4. Ducts or channels 5 and 6 are provided in the bottom part 4 for respectively receiving measuring gas and fuel gas, such as $H_2$. The two ducts 5 and 6 are interconnected in the bottom part so that the measuring gas and the fuel gas are mixed therein.

Reference numeral 7 denotes a common continuation duct of the ducts 5 and 6 so that the measuring gas fuel gas mixture passes through the duct 7 and into a burner nozzle 8. Air needed for combustion passes into and through a duct 9 in bottom part 4, and from there into the interior of housing or case part 3. The lower portion of that case part 3 includes a pot-like insert 11 whose bottom is disposed above bottom part 4 and is provided with passages 10 for air. The air thus flows into the pot-like part 11, around nozzle 8, and toward nozzle tip 12. The nozzle tip projects slightly above pot 11.

The nozzle 8 projects from a base of a somewhat larger diameter, and that base is held between bottom part 4 and the bottom of pot 11 by means of electrically insulating spacers 13. The nozzle and these parts 11 and 4 and others are made of metal, but the nozzle member 8 is electrically insulated from the case structure by spacers 13.

Reference numeral 15 refers to a tubular target electrode which is coaxially disposed to but above nozzle 8. This target electrode 15 is held on internal ledges of case part 3 and cover 2 by means of annular, electrically insulating spacers 17.

The case part 3 is provided with two ducts 19 and 20, leading into the interior of that case part, for purposes of running wires to the electrically active parts in the detector; these are the nozzle 8 (to whose base one wire is affixed) and the target electrode 15.

The cover 2 has a chamber which is in alignment with the hollow interior of case part 3, and an exhaust duct 18 communicates therewith.

Figure 2:
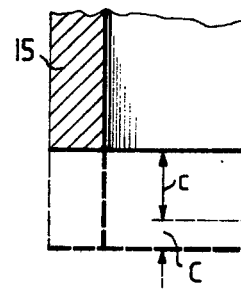
FIG. 2 is an enlarged section view of the burner nozzle in FIG. 1.
Figure 2:
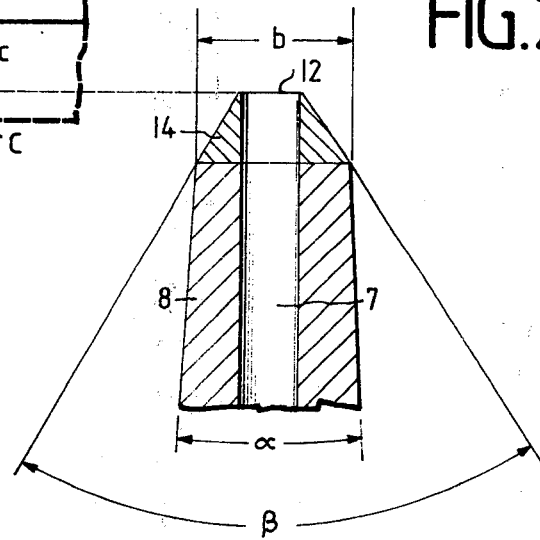

After having described the general layout, we now turn to particulars in the construction. All of the case parts 2, 3 and 4, the pot-shaped insert 11, and the nozzle 8 are made of stainless steel. The stem of nozzle 8 is slightly conically tapered, the cone angle $\alpha$ being up to 14° (see FIG. 2). The tip element 14 for the nozzle is made of a platinum metal, or an alloy such as platinum-iridum, and is welded to the nozzle stem. Tip 14 is likewise concial (strictly speaking, frustoconical) in shape, with an apex cone angle $\beta$ of 60°. The base of tip element 14 has a diameter b of 1 mm. It was found that for reasons of operation diameter b should not be larger. Also, cone angle $\beta$ of the nozzle should not exceed 90°. The duct 7 through the nozzle should have a diameter of from 0.3 mm ot 0.5 mm.

The target electrode 15 is also made of platinum and has an inner diameter in the range of from 6 mm to 15 mm. The target electrode may, in the alternative, be comprised of a glass or ceramic tube which is coated with a noble metal, such as platinum. The length of electrode 15 is preferably 30 mm.

The lower end of electrode 15 is shown to be disposed slightly above nozzle tip 12 proper (spacing c). This is shown in greater detail in FIG. 2. However, the plane of tip 12 and the plane of the lower electrode may coincide, or the tip may actually project a little into the tubular target electrode ($-c$). It was found that the maximum distance and spacing in axial direction is approximately 15 mm, while the maximum tip penetration into target 15 is approximately 3 mm. In other words, the nozzle tip can have a distance c from the lower end plane of electrode 15 of from $-3$ mm to $+15$ mm. That range defines the permissible range for purposes of a practical desired measuring accuracy.

The insulating spacers 17 should be made of oxide-ceramic material. If the wall temperature does not exceed 150° C., one may also use polytetrafluorethylene. The entire device should be subjected to a thermostatic temperature control (not illustrated) in a conventional manner to make sure that temperature variations do not result in changes in the measurements and the operating characteristics.

A voltage of at least 200 volts is applied between the nozzle 8 and electrode 15. The amount of gas passing through, i.e., the flow rate, is critical for the accuracy of measurement. As to the measuring gas, it is 2–10 Nml/min (milliliters per minute at 760 torr and 0° C.), for the combustion air 200 to 250 Nml/min, and for the fuel gas ($H_2$) 42 to 48 Nml/min. The fuel gas may be diluted with helium, but the flow rate of helium should not exceed 70 Nml/min.

It was found that a flow meter constructed within the prescribed rules and operated with the stated parameters is sufficiently accurate and will not exhibit the drawbacks outlined above.

The invention is not limited to the embodiments described above; but all changes and modifications thereof, not constituting departures from the spirit and scope of the invention, are intended to be included.

We claim:

1. A flame ionization detector, comprising:
   a cylindrical case having a bottom part and a hollow interior;
   first duct means for supplying fuel gas and a measuring gas, and mixing same;
   a nozzle member having a internal duct of from 0.3 mm to 0.5 mm and being connected to the first duct means for receiving therefrom the fuel gas as mixed with the measuring gas, said member being of a cylindrical or conical outer configuration with a cone angle not exceeding 14° and having a platinum metal type tip of a conical configuration with a cone angle not exceeding 90°, but larger than the cone angle of the member itself, the base of that conical member having a diameter not exceeding 1 mm;
   a tubular target electrode disposed inside said case in concentric relation to said nozzle member, the nozzle tip being disposed near a lower end of the target electrode at a distance therefrom at less than approximately 15 mm, but penetrating the electrode not deeper than approximately 3 mm;
   means for supplying voltage to said target electrode and said nozzle member, the target electrode and the nozzle member being insulated from each other; and
   means for supplying combustion air to said case.

2. The detector as in claim 1, said target electrode having a surface of a noble metal.

3. The detector as in claim 2, said target electrode being made of a noble metal.

4. The detector as in claim 2, said target electrode being made of a carrier covered by a noble metal.

5. The detector as in claims 1 or 2, said lower end of the target electrode being spaced from the nozzle tip and by not more than 15 mm.

6. A method of measuring the concentration of hydrocarbons in a measuring gas, comprising the steps of using a detector as in claim 1;
   providing a measuring gas flow of from 2 milliliter/min to 10 milliliter/min, combustion air of from 200 milliliter/min to 250 milliliter/min, and $H_2$ of from 42 milliliter/min to 48 milliliter/min, all volumes normalized for 760° and 0° C.

7. A method as in claim 6, including the step of diluting $H_2$ by He, at a constant flow of He not exceeding 70 Nml/min.

* * * * *